(12) United States Patent
Larkner et al.

(10) Patent No.: US 12,011,524 B2
(45) Date of Patent: Jun. 18, 2024

(54) PLATELET AGITATOR WITH DISCONTINUOUS USER INPUT CONTROLS

(71) Applicant: HELMER SCIENTIFIC, LLC, Noblesville, IN (US)

(72) Inventors: Thomas J. Larkner, Noblesville, IN (US); Heather Barry, Indianapolis, IN (US)

(73) Assignee: HELMER SCIENTIFIC, LLC, Noblesville, IN (US)

( * ) Notice: Subject to any disclaimer, the term of this patent is extended or adjusted under 35 U.S.C. 154(b) by 990 days.

(21) Appl. No.: 16/966,999

(22) PCT Filed: Feb. 1, 2019

(86) PCT No.: PCT/US2019/016286
§ 371 (c)(1),
(2) Date: Aug. 3, 2020

(87) PCT Pub. No.: WO2019/152800
PCT Pub. Date: Aug. 8, 2019

(65) Prior Publication Data
US 2021/0038781 A1    Feb. 11, 2021

Related U.S. Application Data

(60) Provisional application No. 62/625,558, filed on Feb. 2, 2018.

(51) Int. Cl.
*A61M 1/00*    (2006.01)
*A61M 1/02*    (2006.01)

(52) U.S. Cl.
CPC ..... *A61M 1/025* (2013.01); *A61M 2202/0427* (2013.01); *A61M 2205/18* (2013.01); *A61M 2205/36* (2013.01); *A61M 2205/502* (2013.01); *A61M 2205/52* (2013.01)

(58) Field of Classification Search
None
See application file for complete search history.

(56) References Cited

U.S. PATENT DOCUMENTS

| | | | | |
|---|---|---|---|---|
| 5,674,741 | A | * 10/1997 | Watanabe | B65C 9/1884 156/503 |
| 7,638,100 | B2 | * 12/2009 | Dawes | A61M 1/025 422/536 |
| 2002/0011923 | A1 | 1/2002 | Cunningham et al. | |
| 2014/0043930 | A1 | 2/2014 | Bell et al. | |
| 2015/0037225 | A1 | 2/2015 | Cordisco | |
| 2018/0147306 | A1 | * 5/2018 | Crawley | A61M 1/025 |

FOREIGN PATENT DOCUMENTS

WO    WO2016/084001    6/2016

OTHER PUBLICATIONS

PCT Search Report and Written Opinion prepared for PCT/US2019/016286, completed Jul. 31, 2019.

* cited by examiner

*Primary Examiner* — Anshu Bhatia
(74) *Attorney, Agent, or Firm* — Womble Bond Dickinson (US) LLP

(57) ABSTRACT

A platelet agitator includes a base and a frame. The frame moves laterally relative to the base at variable speeds. The agitator further includes a controller and a user interface in communication with the controller. The user interface has a discontinuous input device that has at least a portion of adjustment range that is non-linear compare to the remainder of the adjustment range.

29 Claims, 9 Drawing Sheets

```
Green_Zone_Graphic_Start_Position = 4/6;
Green_Zone_Graphic_End_Position = 5/6;
Minimum_Speed = 40;
Maximum_Speed = 80;                                                   } 98
Min_ADC_Counts = 20;
Max_ADC_Counts = 4095;
Green_Zone_Speed = 72
Maximum_Low_Linear_Zone_Speed = Green_Zone_Speed - 1;
Minimum_High_Linear_Zone_Speed = Green_Zone_Speed + 1;
Full_Range_Counts = Max_ADC_Counts - Min_ADC_Counts;
Green_Zone_Begin_Counts = Green_Zone_Graphic_Start_Position * Full_Range_Counts;
Green_Zone_End_Counts = Green_Zone_Graphic_End_Position * Full_Range_Counts;
Begin_Low_Linear_Zone_Counts = Min_ADC_Counts;
End_Low_Linear_Zone_Counts = Green_Zone_Begin_Counts - 1;
Begin_High_Linear_Zone_Counts = Green_Zone_End_Counts + 1;
End_High_Linear_Zone_Counts = Max_ADC_Counts;
Low_Linear_Range_Total_Counts = End_Low_Linear_Zone_Counts - Begin_Low_Linear_Zone_Counts;
High_Linear_Range_Total_Counts = End_High_Linear_Zone_Counts - Begin_High_Linear_Zone_Counts;
Low_Linear_Range_of_Speeds = Maximum_Low_Linear_Zone_Speed - Minimum_Speed;
High_Linear_Range_of_Speeds = Maximum_Speed - Minimum_High_Linear_Zone_Speed;
Low_Linear_Counts_Per_Speed_Increment = Low_Linear_Range_Total_Counts/Low_Linear_Range_of_Speeds;
High_Linear_Counts_Per_Speed_Increment = High_Linear_Range_Total_Counts/High_Linear_Range_of_Speeds;
```

FIG. 6

PLATELET AGITATOR WITH DISCONTINUOUS USER INPUT CONTROLS

CROSS-REFERENCE TO RELATED APPLICATIONS

This application is a national stage entry under 35 USC § 371 of PCT International Application Number PCT/US2019/016286 filed Feb. 1, 2019, which claims priority under 35 U.S.C. § 119(e) to U.S. Provisional Application Ser. No. 62/625,558 filed on Feb. 2, 2018, the entire disclosures of both of which are incorporated herein by reference.

TECHNICAL FIELD

The present disclosure relates to a platelet agitator. More specifically, the present disclosure relates to a platelet agitator having an input device and a value selection guide that has a discontinuous response to user inputs.

BACKGROUND

Platelets are one of several products yielded from whole blood and used in the medical field. Typically, platelets have a storage life of five days. For best quality, platelets may be agitated at a particular speed to maintain the suspension of the platelets in the storage medium. This agitation is accomplished through oscillation of trays, drawers, or compartments used for storage of the platelets. Lack of oscillation or oscillation at an improper speed may result in reduced yield of platelets or a reduced acceptable storage life.

Additionally, it has been found advantageous to maintain the rate of agitation at a definitive speed set by a user. The definitive speed of agitation is accomplished through the selection of a speed by the user using an input device. Inability to maintain a definitive speed of agitation may result in reduced yield of platelets or reduced acceptable storage life.

SUMMARY

The present disclosure includes one or more of the features recited in the appended claims and/or the following features which, alone or in any combination, may comprise patentable subject matter.

According to a first aspect of the present disclosure, an agitator for oscillation of platelets comprises a base; a frame that oscillates relative to the base at variable speeds, a controller, and a user interface device including a user input device in communication with the controller and operable to receive an input from a user and a value selection guide coupled to the user input device and displays a range of oscillation speeds for the frame.

In some embodiments, the value selection guide includes at least one discontinuous single state zone.

In some embodiments, the at least one discontinuous single state zone is a constant value over a subset of a total rotational range.

In some embodiments, the at least one discontinuous single state zone is a constant value over a subset of a total range.

In some embodiments, the user interface is provides both a range of analog continuously changing values and an at least one discontinuous single state zone.

In some embodiments, the at least one discontinuous single state zone is located between a first range of analog continuously changing values and a second range of analog continuously changing values.

In some embodiments, the agitator further comprises a memory device in communication with the controller and stores data from a plurality of sensors coupled to the agitator.

In some embodiments, each of the plurality of sensors are in communication with the controller and are communicates an independent speed to the controller.

In some embodiments, the base includes a motor, an output shaft coupled to the base, and an arm pivotably coupled to the motor and moves the frame relative to the base.

In some embodiments, the controller is monitors and controls the oscillation speed of the agitator frame relative to the agitator base.

In some embodiments, the agitator is oscillated at a rate that is sufficient to prevent coagulation of the platelets located in the agitator.

In some embodiments, the agitator includes a sensor in communication with the controller and the controller is monitors the speed of oscillation of the frame of the agitator relative to the base of the agitator.

In some embodiments, the controller is stores a log of events.

In some embodiments, the log includes the date of the event, the time of the event, and the measured speed of oscillation of the agitator during the event.

According to a second aspect of the present disclosure, an agitator, comprises a base, a frame coupled to the base and oscillates relative to the base, a controller, a memory device in communication with the controller, a user interface device including a user input device in communication with the controller and operable to receive input from a user and a value selection guide coupled to the user input device and displays a range of oscillation speeds, and at least one sensor in communication with the controller.

In some embodiments, the controller comprises a processor and the memory device includes instructions that, when executed by the processor, cause the controller to control the speed of oscillation of the frame relative to the base.

In some embodiments, the processor uses a feedback control system to control the speed of oscillation of the frame relative to the base.

In some embodiments, the feedback control system is a proportional-plus-integral-plus-derivative controller.

In some embodiments, an event is logged if the agitator frame fails to oscillate at an acceptable speed relative to the agitator base.

In some embodiments, the user may input an at least one alarm condition for an operational parameter and the controller logs an event if the alarm condition is met.

In some embodiments, the user may input the at least one alarm condition for the speed of oscillation of the frame relative to the base.

According to a third aspect of the present disclosure, a control system for a variable speed device comprises a controller having a processor and a memory device, a variable speed driver in communication with the controller, and a user input device have a range of adjustments, the range of adjustments being discontinuous such that a portion of the range is linear and a portion of the range is non-linear. The controller receives a signal from user input device and, in response, the processor processes the signal using instructions from the memory device and provides a signal to the variable speed driver to drive the variable speed driver at the speed selected with the user input device.

In some embodiments, the speed is changed linearly through the linear portion of the range of the user input device.

In some embodiments, the speed is maintained at a constant speed through the non-linear portion of the range.

According to a fourth embodiment of the present disclosure, a control system for a variable input device comprise a controller having a processor and a memory device, a variable output device in communication with the controller, and a user input device have a range of adjustments, the range of adjustments being discontinuous such that a portion of the range is linear and a portion of the range is non-linear. The controller receives a signal from user input device and, in response, the processor processes the signal using instructions from the memory device and provides a signal to the variable output device to control the variable output device at the input selected with the user input device.

In some embodiments, the variable output is changed linearly through the linear portion of the range of the user input device.

In some embodiments, the variable output is maintained at a constant rate through the non-linear portion of the range.

In some embodiments, the variable output is maintained at a constant rate through the non-linear portion of the range.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 6 is an example of pseudo code for initialization of the input device in FIGS. 1 and 2;

DETAILED DESCRIPTION

Figure 1:
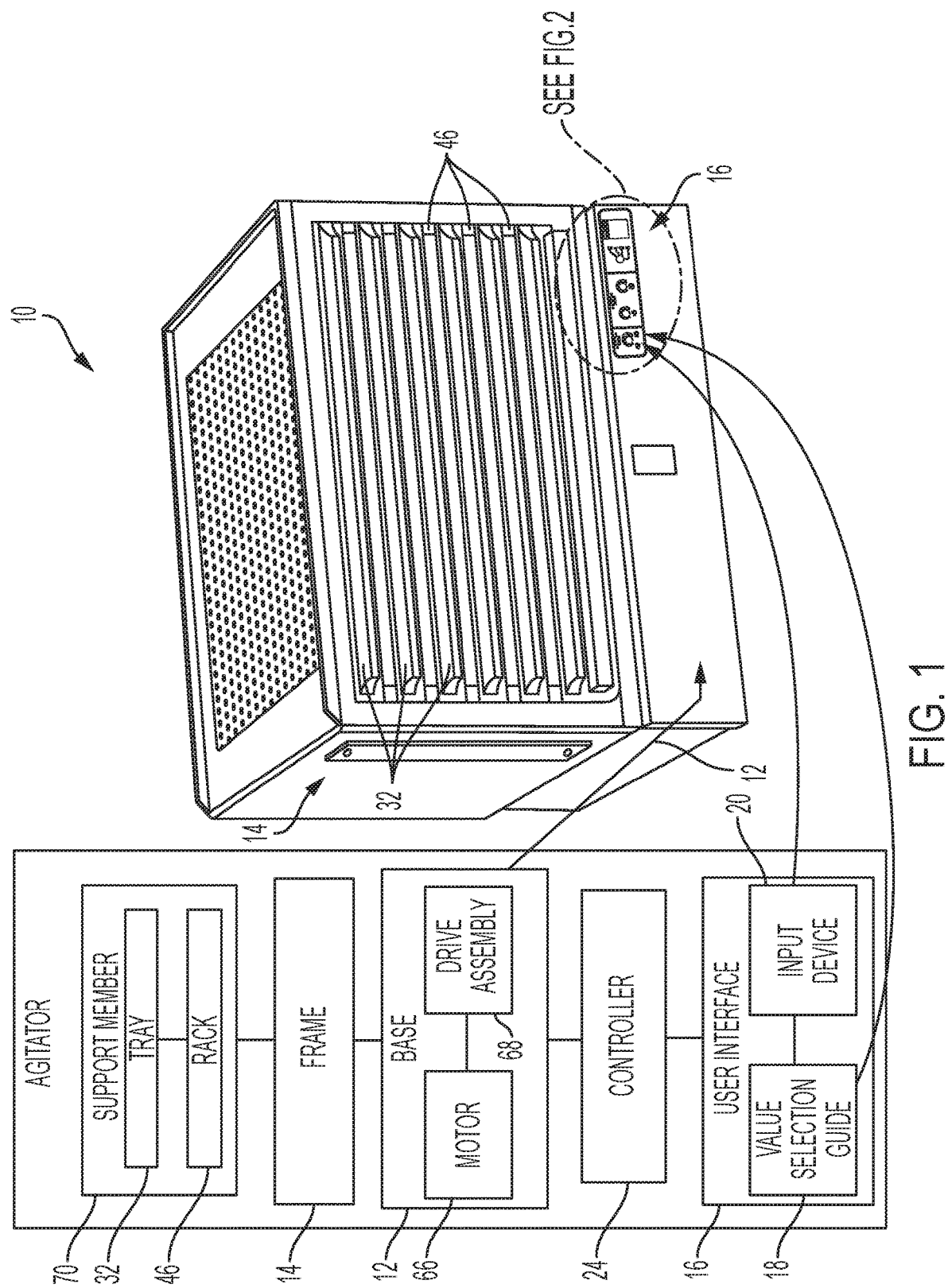
FIG. 1 is a diagrammatic perspective view of a platelet agitator showing a value selection guide and an input device.
Figure 2:
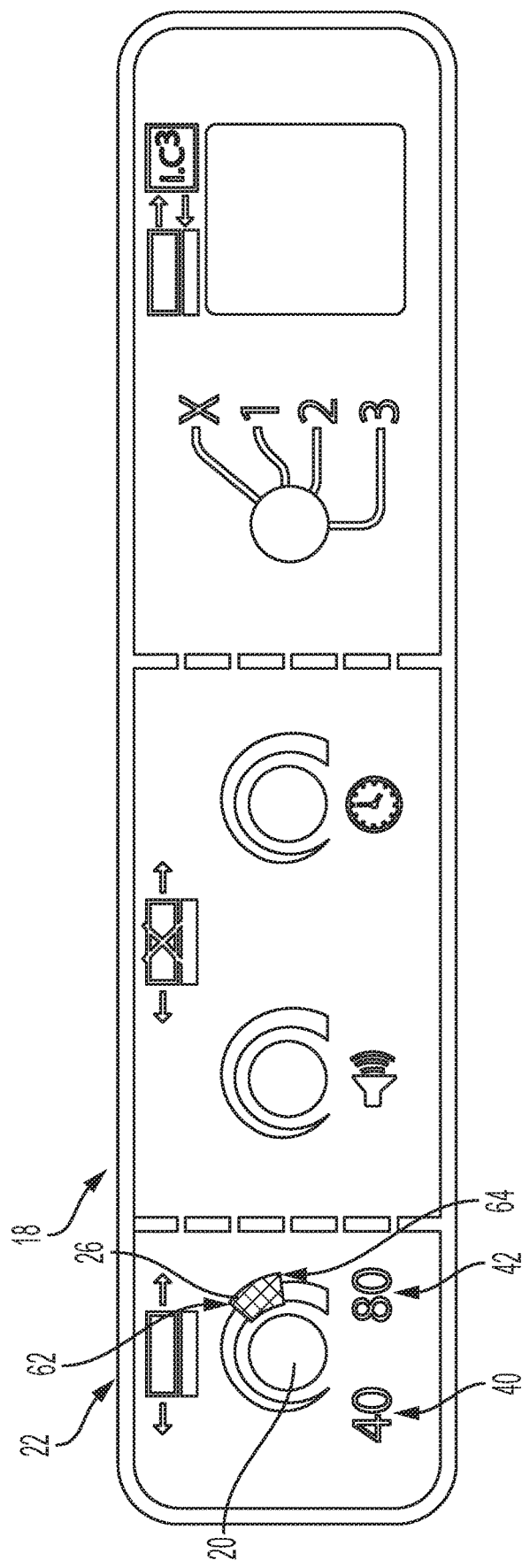
FIG. 2 is an enlarged view of the value selection guide showing a discontinuous single state zone as a subset of a total range of agitator speeds.
Figure 3:
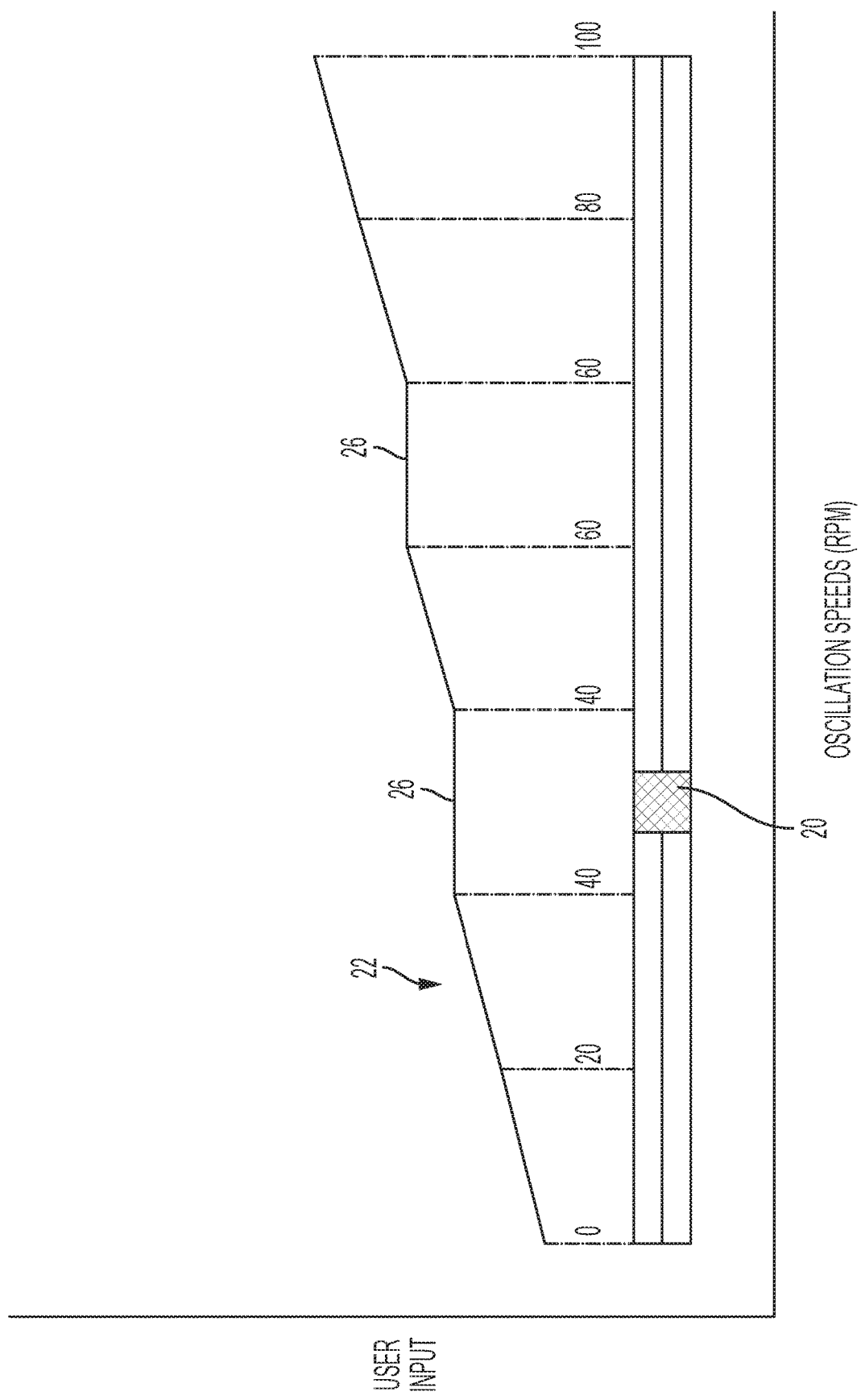
FIG. 3 is a graphical representation showing two discontinuous single state zones flanked by linearly continuous zones.

An agitator 10 in accordance with the present disclosure is adapted for oscillating platelets at a specific, desired speed and providing discontinuous single state zone(s) 26 as shown in FIGS. 1-3. Agitator 10 may be included in an incubator 50 or agitator 10 may be independent of incubator 50. Agitator 10 is configured to operate independently of incubator 50 so that the speed of agitator 10 may be selected by a user interface 16 integrated into agitator 10. User interface 16 is configured to receive user input through an input device 20 configured to include the discontinuous single state zone 26 in which the value selected is constant over a subset of the total range of agitator 10 speeds. User input within discontinuous single state zone 26 ensures proper interpretation of the user input by a controller 24.

Because agitator 10 is configured to operate independently of incubator 50, agitator 10 may be used with a variety of systems and may be obtained as an aftermarket accessory separate from incubator 50. As a result, agitator 10 may be coupled to systems for agitation of other mediums outside that of platelets.

Agitator 10 includes a base 12, a frame 14 coupled to an upper surface of base 12, and a support member 70 configured to support a plurality of containers of platelet samples. Base 12 includes a motor 66 and a drive assembly 68 operable to oscillate frame 14 laterally in relation to base 12. Support member 70 includes a plurality of trays 32 and a plurality of rack members 46 configured to support the trays 32. Illustratively, trays 32 slide on top of rack members 46 so that containers of platelet samples may be placed on trays 32 and slid into a storage position as shown in FIG. 1. Trays 32 are also configured to extend into an open position so that the storage space of trays 32 is accessible by a user.

Illustratively, motor 66 of base 12 is a variable speed DC gear-motor configured to include an output shaft and a speed sensor 30. The motor output shaft is coupled to a frame (not shown) of the base 12 at one end and pivotably coupled to a first end of a crank arm (not shown) of the drive assembly 68 at a second end and configured to provide rotational output to the crank arm. The second end of the crank arm is coupled to the frame 14 so that the motion of the crank arm is transferred to the frame 14 to move the frame 14 relative to the base 12. The speed sensor 30 is in communication with a controller 24, included in agitator 10, to provide a signal to controller 24 indicative of the speed of motor 66 and further configured to sense when frame 14 moves laterally to a position near the speed sensor 30. Illustratively, the speed sensor 30 is embodied as a proximity switch.

The crank arm is pivotably coupled to motor 66 and is configured to translate the rotational output from the motor output shaft to linear output. The crank arm may be connected to frame 14 such that rotation of motor 66 results in lateral motion of frame 14 relative to base 12. Frame 14 is configured to move laterally relative to base 12 on two slides (not shown). Each revolution of the gear-motor completes an agitation oscillation cycle by moving frame 14 with respect to base 12. This oscillation results in continuous agitation of the platelets, thereby preventing the platelets from clotting When frame 14 moves away from the speed sensor 30, the speed sensor 30 ceases to sense frame 14 and is configured to generate a signal which is transmitted to controller 24. Controller 24 is configured to process the signal from the speed sensor 30 to determine the speed of the oscillations of agitator 10. A Hall-effect proximity switch is used in the illustrative embodiments; however, it should be clear that other apparatuses may be used to monitor the speed of the oscillation of frame 14. For example, in some embodiments, a rate-per-minute (rpm) sensor is coupled directly to the motor output shaft. In other embodiments, a contact switch is used. In further embodiments, the proximity switch may be an optical switch. In other embodiments, the switch may be a reed switch.

Controller 24 is operable to sense if agitator 10 fails to oscillate. In such a case, controller 24 begins a timing sequence based on a time interval input by a user. Once the time interval is reached, controller 24 activates an alarm to inform the user that the oscillations have stopped; controller 24 is further configured to log the alarm for future reference. In some embodiments, controller 24 may be configured directly by means of 16 or indirectly through defined protocol communication with another device.

Agitator 10 further includes a user interface 16 coupled to agitator 10. User interface 16 includes a value selection guide 18 and input device 20; value selection guide 18 and input device 20 are both located on an outer surface of agitator 10 so that the user interface 16 is configured to accept user input and display user input to the user. In other embodiments, user interface 16 may further include a display device 17 configured to display feedback indication of the actual value selected by the user and/or other pertinent information concerning agitator 10.

User interface 16 is in communication with controller 24 to provide inputs to controller 24 and display outputs from controller 24. Illustratively, value selection guide 18 is embodied as a printed label coupled to input device 20, as shown in FIG. 2. Value selection guide 18 includes at least one subsection 22 concerning the speed of agitator 10, illustratively shown in FIG. 2. Subsection 22 is configured to display a range of speed selection values and includes a zone 26 representing a value that is constant over a subset of the total speed selection range. The ranges outside of zone 26 represent analog continuously changing speed selection values whereas zone 26 represents a discontinuous fixed/discrete value range and is further described below. In some embodiments, subsection 22 may include multiple discontinuous fixed value zones 26 as shown in FIG. 3. Illustratively, the multiple discontinuous fixed value zone(s) 26 are indicated on the selection guide using color, symbols, or other known notation methods. As shown in FIG. 2, zone 26 may be identified using the color green and/or placing a rectangle identifying a first end 62 and a second end 64 of zone 26, zone 26 being located between the first end 62 and the second end 64. In embodiments where multiple fixed value zones 26 are present, each different zone 26 will be indicated by a separate identifying indicia spaced apart on the selection guide.

Value selection guide 18 may further include a variety of labels concerning the speed of agitator 10, temperature of agitator 10, audio volume of alarm, alarm trigger time, as well as other measurements concerning the status of agitator 10. In other embodiments, value selection guide 18 may be a monochromatic liquid crystal display (LCD). In some embodiments, value selection guide 18 may be a colored LCD display. In further embodiments, value selection guide 18 may be a graphical user interface with input device(s) 20 integrated in the display.

Input device 20 is coupled to value selection guide 18 so that input device 20 may be positioned by a user at the desired value. Illustratively, input device 20 is embodied as a rotary control switch configured to rotate. As shown in FIG. 2, input device 20 is configured to rotate clockwise in order to change the speed selection value from 40 revolutions per minute (rpm) to 80 rpm. In other embodiments, the range of speed selection values may vary depending on the desired outcome. Furthermore, input device 20 may be embodied as a linear slider control switch, as shown in FIG. 3, configured to move left to right so to change the desired input value. The linear slider control switch may further be configured to move vertically in order to change the desired input value.

In other embodiments, input device 20 may be a non-detent, resistive wiper potentiometer switch. In some embodiments, input device 20 may be a monochromatic liquid crystal display (LCD). In further embodiments, value selection guide 18 may be a colored LCD display. In other embodiments, value selection guide 18 may be a graphical user interface touchscreen knob.

Zone 26 of subsection 22 is configured maintain a set speed when a user places input device 20 within zone 26. Zone 26 is identified on value selection guide 18 so that a user may place input device 20 within zone 26 in order to assure a constant value over a subset of the total range. In doing so, a user is able to select a discontinuous value representing a single, constant speed as indicated on value selection guide 18. Illustratively, as shown in FIG. 2, subsection 22 is configured to display a minimum selection speed 40 of 40 rpm, zone 26 as a constant 72 rpms, and a maximum selection speed 42 of 80 rpm. The range of values between minimum selection speed 40 and the first end 62 of zone 26 are configured to be measured by controller 24 as linearly increasing until reaching the first end 62 of zone 26. Therefore, when a user places input device 20 between minimum selection speed 40 and the first end 62 of zone 26, the speed of agitator 10 increases linearly in single digit speed increments so that a single speed increment represents a single value.

Zone 26 is defined as a discontinuous single state or value control parameter so that even if input device 20 moves within zone 26, the value zone 26 is the constant. Illustratively, as shown in FIG. 2, zone 26 covers a range of approximately ⅙ of the total travel. Similar to the range of values between minimum selection speed 40 and the first end 62 of zone 26, the range of values between the second end 64 of zone 26 and maximum selection speed 42 are configured to be measured by controller 24 as linearly increasing, once input device 20 is placed outside of zone 26. Minimum selection speed 40, zone 26, and maximum selection speed 42 may be changed by programming alternative values or varying responses to certain values resulting in a broad spectrum of possible values of minimum selection speed 40, zone 26, and maximum selection speed 42 as shown in FIG. 2. Illustratively, as shown in FIG. 6, values 98 are configured to be changed in order to quickly adjust the location of zone 26 and/or the overall speed range and/or the analog-to-digital resolution available. Furthermore, additional zones 26 may be programmed into controller 24 as shown in FIG. 3, in which case each discontinuous zone 26 covers a range of approximately ⅐ of the total travel.

Maintaining a single discontinuous zone 26 (illustrated in FIG. 2) or multiple discontinuous zones 26 (illustrated in FIG. 3) provides a larger target area to the user for placement of input device 20 to achieve a pre-defined target speed. The pre-defined target speed is a speed at which the operation of the agitator 10 is optimized for agitating the particular materials that are planned to be stored in the agitator 10. In this way, the user does not have to fine tune the speed input, but rather has the option to set the user input device 20 at the optimized target. As such, the speed can be adjusted through a linear range, but may be easily set to the optimal speed by selecting the discontinuous zone 26. Illustratively, input device 20 may be placed in the approximate middle of the desired discontinuous zone 26 to ensure a proper interpretation and response by the control system.

Controller 24 is part of a control system shown in FIG. 4 and described in further detail below. Controller 24 comprises a processor based system which includes software to perform computations. The illustrative embodiments utilize an analog-to-digital (ADC) control routine 200 to convert input from input device 20 and speed sensor(s) 30 to the desired operation, as shown in FIG. 5. However, it should be understood that there are a number of feedback control schemes which may be utilized to control the speed of agitator 10.

A sensor 30 is located within agitator 10 and is in communication with controller 24 to provide a signal representative of the speed of agitator 10. Controller 24 is operable to process the signal of the speed of agitator 10 from sensor 30 to determine the actions necessary to adjust the speed of the agitator 10 in response to input from the user and/or sensor 30. Sensor 30 is also in communication with a speed chart recorder 36 shown in FIG. 4 and described in detail below. In some embodiments, multiple sensors 30 may be located throughout agitator 10 with each sensor 30 configured to communicate an independent speed to controller 24. Controller 24 is configured to process all of the speed signals so that average rate at which frame 14 is oscillating in relation to base 12 is determinable. In some embodiments, speed sensor 30 used by controller 24 to control the speed of agitator 10 may be different than sensor 30 used to monitor alarms. Sensors 30 may be configured to control the temperature of agitator 10, the annunciation volume, the audible alarm volume setting, an audible alarm trigger time setting, and other considerations as can be reasoned by those skilled in the art.

The controller 24 includes a processor (not shown) that is in communication with a memory device 28. Instructions for the operation of various aspects of the agitator 10 are stored in memory device 28 and executed by the processor as described herein. In illustrative embodiments, upon processing the speed signal(s) from sensor(s) 30, the processor located within controller 24 is provides at least one full count for each single digit increment in the speed of agitator 10; more full counts per single digit increment are preferred for less positional sensitivity. Within the full count range of the ADC control routine, one or more contiguous portions of the full count range normally attributed to linear incrementing of the input value are instead defined to be interpreted by the control system as a discontinuous single state or value control parameter. This results in a larger fixed zone of constant speed embedded within a subset of possible selections. Illustratively, the user selects the center of the fixed zone to ensure the desired fixed value is accurately conveyed to and understood by the control system while still allowing other allowable speeds to be set by analog.

The processor of the controller 24 may be embodied as any type of processor capable of performing the functions described herein. For example, the processor may be embodied as a single or multi-core processor(s), a single or multi-socket processor, a digital signal processor, a graphics processor, a microcontroller, or other processor or processing/controlling circuit. Similarly, the memory device 28 may be embodied as any type of volatile or non-volatile memory or data storage capable of performing the functions described herein. In operation, the memory device 28 may store various data and software used during operation of the controller 24 such as operating systems, applications, programs, libraries, and drivers. The memory device 28 is communicatively coupled to the processor.

In other embodiments, controller 24 may be in communication with a heating element, a fan, a refrigeration compressor, and a sound device 78 and configured to adjust the temperature of agitator 10, the annunciation volume, the audible alarm trigger time, and many other consideration as can be reasoned by those skilled in the art. In some embodiments, separate and independent temperature sensors may be coupled to a temperature chart recorder and the controller 24. In some embodiments, separate and independent temperature sensors may be used to monitor and control the temperature within agitator 10; one of the temperature sensors being configured to monitor the temperature and another one of the temperature sensors configured to control the temperature.

Figure 4:
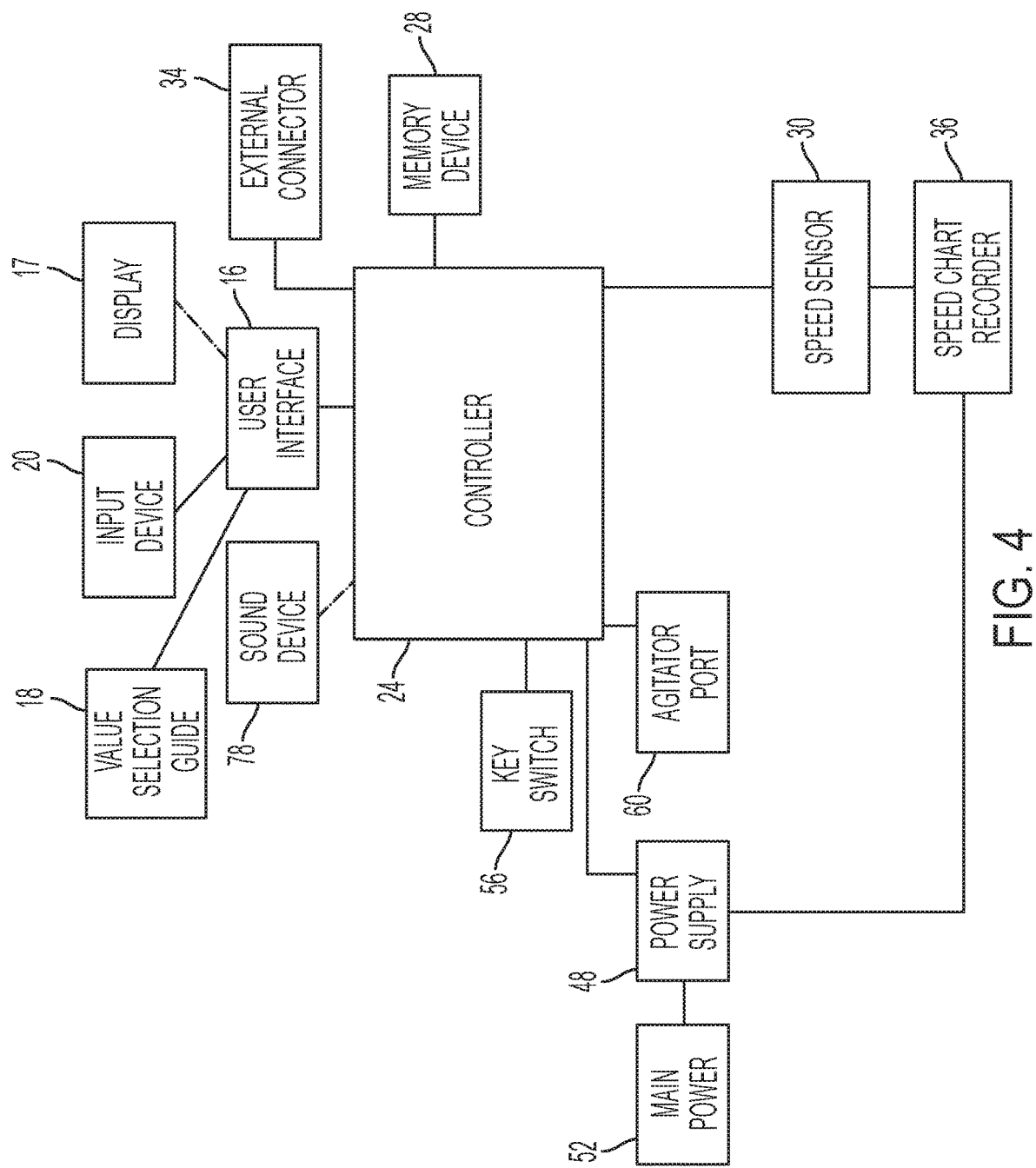
FIG. 4 is a diagrammatic view of a control system of the platelet agitator of FIG. 1.
Figure 5:
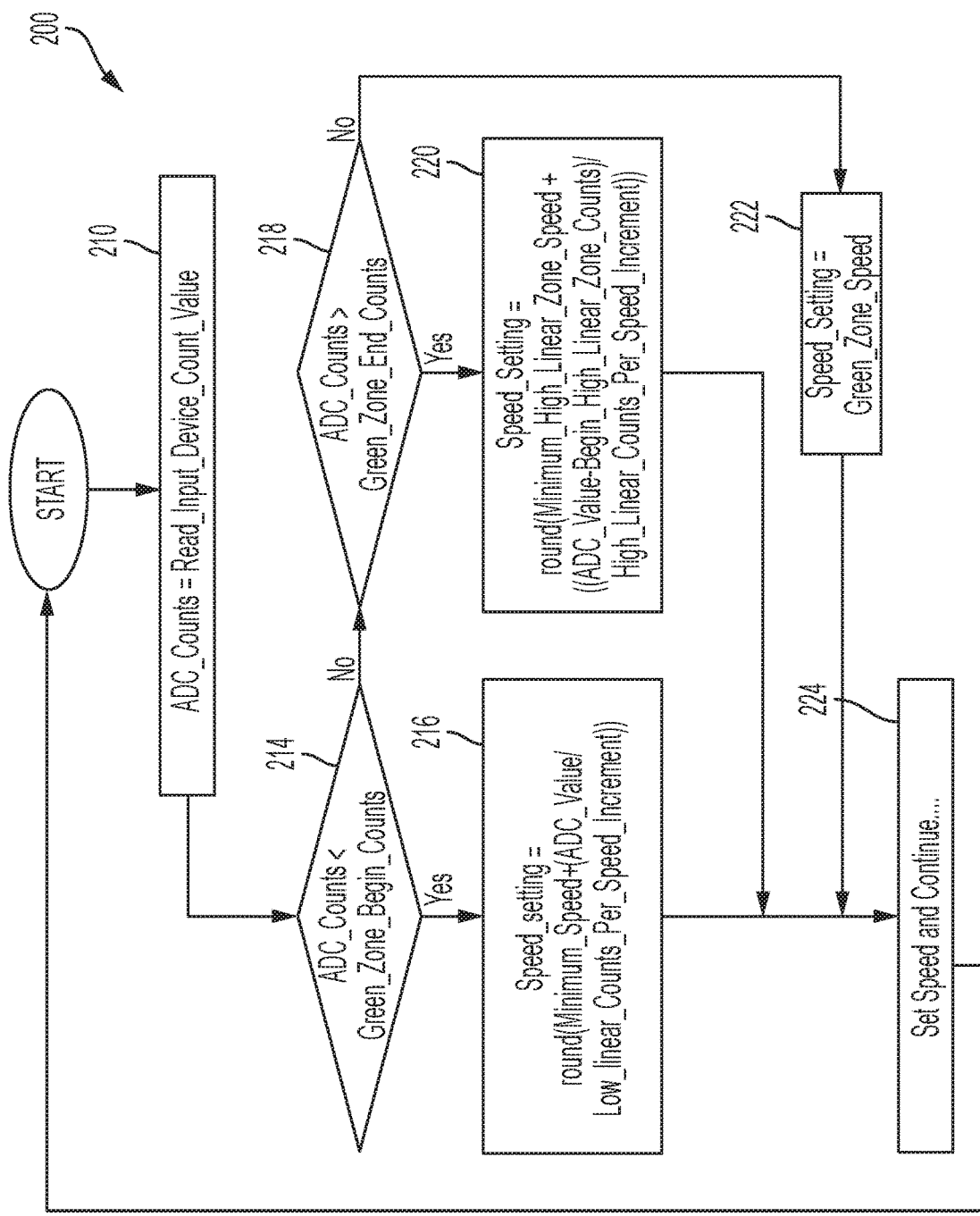
FIG. 5 is a flow chart of a control routine for control of the oscillation speed of the agitator in response to a user input.

As shown in FIG. 4, controller 24 receives power from a power supply 48 which conditions and controls power from a main power source 52. Main power source 52 can be configured to provide any range of AC power from 100-240 Vac, 50/60 Hz. Power supply 48 converts the power as necessary and provides the proper voltage and current to controller 24, a speed control unit 58, and a speed chart recorder 36.

Controller 24 is in communication with an agitator port 60; agitator port 60 is an electrical connection between controller 24 and agitator 10 which allows agitator 10 to communicate agitator's 10 speed in rpms and the total cycles that agitator 10 has completed to controller 24. The communication between controller 24 and agitator 10 further serves to start and stop agitation. A single revolution of motor 66 results in a single cycle of oscillation of agitator 10. Information concerning the speed and cycles of agitator 10 is processed by controller 24 and if an alternate embodiment of user interface 16 includes a display or wireless output, said information is accessible to a user through user interface 16; the information is also stored in a memory device 28 in communication with controller 24.

Controller 24 is also in communication with a key switch 56 as shown in FIG. 4. Key switch 56 is a mechanical switch that requires a key to actuate the switch between an on position and an off position. In the on position, key switch 56 closes an electrical circuit which enables controller 24, agitator 10, and incubator 50 to operate. When key switch 56 is in the off position, the electrical circuit is open making controller 24, agitator 10, and incubator 50 inoperable.

Illustratively, controller 24 is in communication with a memory device 28, which stores software used by controller 24 and stores data related to the operation of agitator 10 which is in communication with controller 24. Controller 24 is also in communication with an external connector 34 which permits a user to access memory device 28 to update software or to download information stored by controller 24.

Referring to FIG. 5, a control routine 200 for the determination and control of the speed of oscillation of agitator 10 is shown. Step 210 in control routine 200 represents a commencement step which occurs upon start-up of agitator 10 and is followed by step 212 where control routine 200 receives the user input for the desired speed of agitator 10. In step 214, it is determined whether the user input is slower than that of the discontinuous zone 26. If so, then the speed is determined in step 216 so that the speed of agitator 10 is outside and below that of zone 26. If the user input is not slower than zone 26, then control routine 200 initiates step 218 to determine if the user input is greater than that of zone 26. If so, then the speed is determined in step 220 so that the speed of agitator 10 is outside and above that of zone 26. If the user input is not faster than zone 26, then the speed is determined in step 222 so that the speed of agitator 10 is within zone 26. In order to set the desired speed, control routine 200 then moves to step 224. After doing so, control routine 200 returns to step 210; control routine 200 thereby continuously monitors the speed of agitator 10 during the operation of agitator 10.

Figure 7:
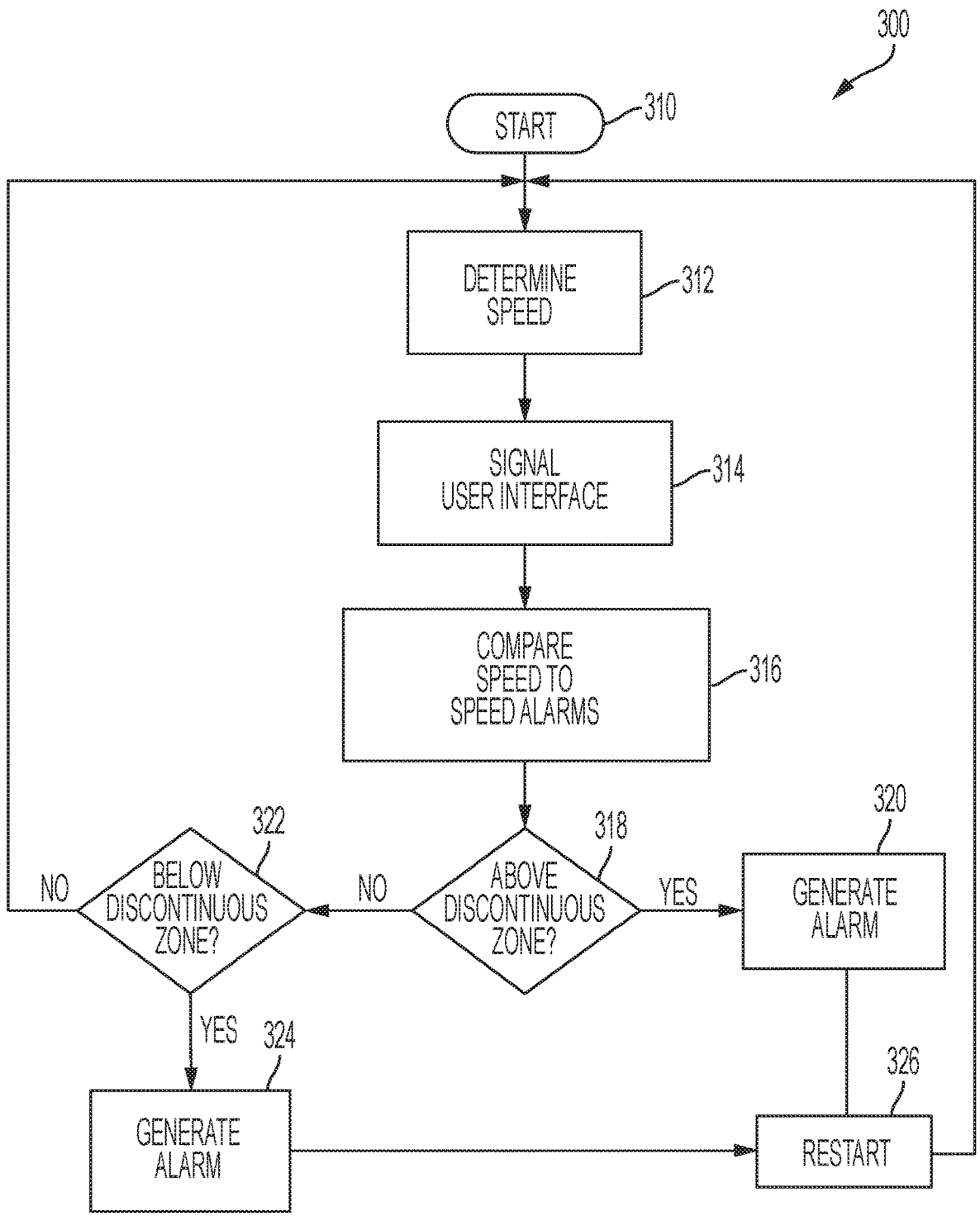
FIG. 7 is a flow chart of a control routine for the monitoring and displaying of the oscillation speed and oscillation speed alarms for the agitator.

A control routine 300 is shown in FIG. 7 and is configured to run when discontinuous zone 26 is selected by via input device 20. If the speed selected is in an acceptable zone outside of discontinuous zone 26, then control routine 300 does not apply. Illustratively, a similar control routine to that of control routine 300 may be configured to apply when an acceptable zone outside of discontinuous zone 26 is selected, but it would have a wider range of variability due to the reduced range of ADC values relating to the speed selection.

The purpose of control routine 300 is to provide a detailed history of the alarms experienced by agitator 10 so that a user may evaluate the operation of agitator 10 and determine if agitator 10 is operating properly and safely preserving the blood products stored therein. Control routine 300 commences at step 310 upon start-up of agitator 10 and advances to step 312 where the current speed of agitator 10 is determined. Step 312 determines the speed by controller 26 which receives a signal from the speed sensor, converts the signal from analog to digital, and processes the digital signal indicative of the speed of agitator 10.

Once the speed is determined, controller 26 progresses to step 314 where the value of the speed is passed to user interface device 16 as a digital signal which is then converted by the user interface device 16 to create a numeric representation of the temperature on optional display device 17.

Figure 8:
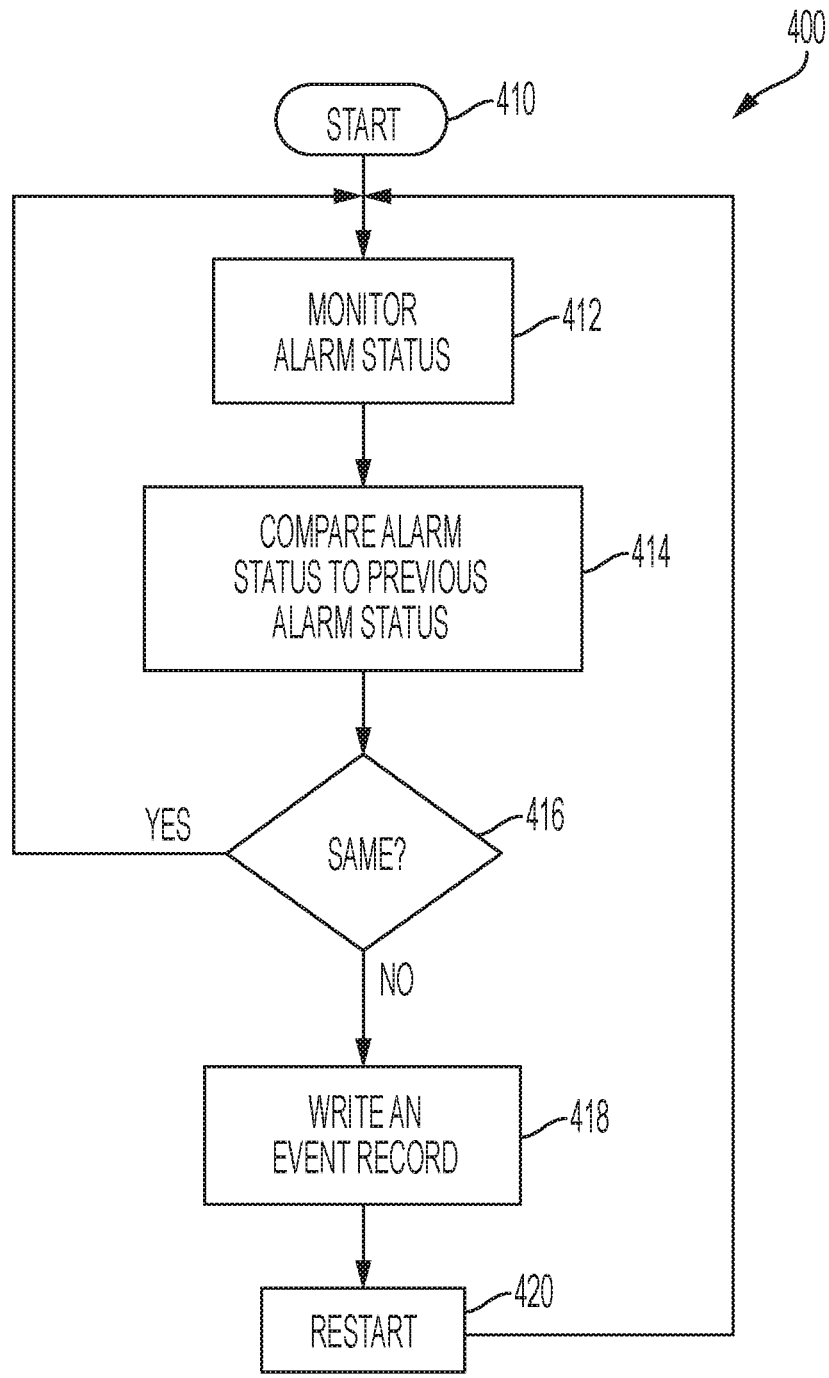
FIG. 8 is a flow chart of a control routine for the monitoring, displaying, and logging of alarms associated with the agitator.
Figure 9:
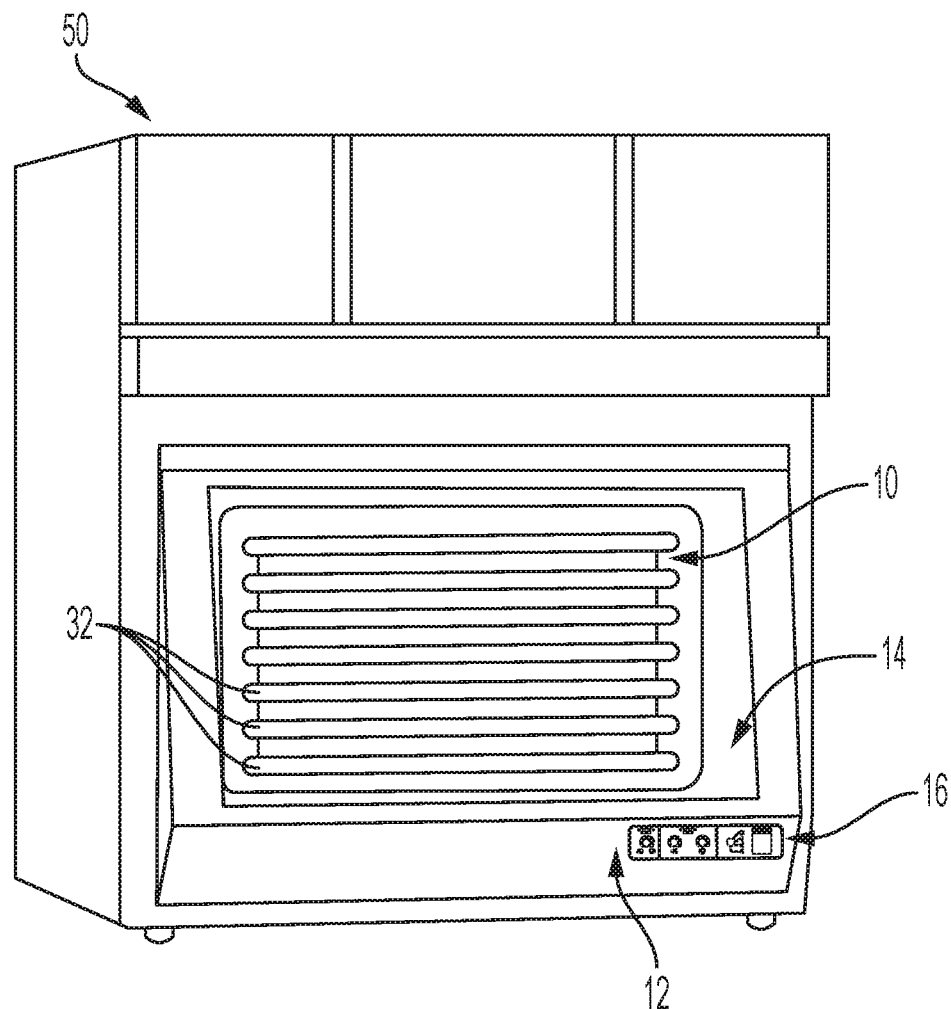
FIG. 9 is an additional embodiment of FIG. 1, showing the agitator located inside of an incubator.

Control routine 300 then progresses to step 316 where the speed is compared to the alarms set by the user. At step 318, control routine 300 evaluates the speed to an upper limit of discontinuous zone 26. If the speed is above the high limit, control routine 300 advances to step 320 where a high speed alarm is generated. Generation of the high speed alarm results in a signal to display device 17 of user interface device 16 which provides a visual indication of the alarm. Additionally, an audible output device is signaled to generate an audible alarm and the alarm is logged by the control routine 400 as shown in FIG. 8. Control routine 300 then progresses to step 326 which results in a restart of control routine 300.

As shown in FIG. 7, if the determination at 318 is that the speed is not above discontinuous zone 26, then control routine 300 advances to step 322 which compares the speed to a lower limit of discontinuous zone 26. If the speed is below discontinuous zone 26, control routine 300 is advanced to step 324 which results in the generation of an alarm similar to step 320 discussed above. Namely, a visual alarm is signaled to optional display device 17, an audible alarm is signaled to the sound device, and the alarm will be logged by control routine 400. Once the alarm has been generated, control routine 300 advances to step 326 which results in a restart of control routine 300. In the event that the speed is not below the lower limit of discontinuous zone 26 at step 322, then control routine 300 returns to step 312 to complete another iteration of control routine 300.

In some embodiments, controller 24 is configured to run an event log control routine 400 is shown in FIG. 8. The purpose of event log control routine 400 is to provide a detailed history of the alarms experienced by agitator 10 so that a user may evaluate the operation of agitator 10 and determine if agitator 10 is operating properly and safely preserving the blood products stored therein. Event log control routine 400 commences at step 410 upon start-up of agitator 10 and advances to step 412 where the current status of all alarms within agitator 10 is determined.

Control routine 400 then advances to step 414 where the alarm statuses are compared to the previous alarm statuses in the previous loop. At step 416, a branch decision is made. If the alarm statuses are the same, control loop 400 returns to step 412 to complete another loop of control routine 400. If the alarm statuses are not the same, then control routine 400 advances to step 418 which results in an event record being generated and written to memory. The event record includes a serial identifier, a status identifier, namely, whether it is the beginning or ending of the event, the date of the event status logged, the time of the event status logged, the speed of agitator 10 at the time of the log entry, and a code identifying the type of event. Types of events logged include high speed of agitator, low speed of agitator, door open, high storage compartment temperature, low storage compartment temperature, high refrigeration compressor temperature, low battery, no battery, mains power failure, and agitator failure. Control routine 400 operates continuously during the operation of agitator 10 such that the event log includes all events which occur.

Although this disclosure refers to specific embodiments, it will be understood by those skilled in the art that various changes in form and detail may be made without departing from the subject matter set forth in the accompanying claims.

What is claimed is:

1. An agitator for oscillation of platelets, the agitator comprising:
   a base;
   a frame;
   a driver configured to oscillate the frame relative to the base at variable oscillation speeds;
   a user input device that is actuatable through a range of positions that correspond to a range of available oscillation speeds for the frame, wherein the range of positions includes a discontinuous single state zone in which a plurality of adjacent positions of the range of positions correspond to a single oscillation speed for the frame; and
   a controller in communication with the user input device and the driver such that the controller is configured to receive a signal from the user input device corresponding to a selected oscillation speed from the range of oscillation speeds and, in response, provide a signal to the driver to operate at the selected oscillation speed.

2. The agitator of claim 1, wherein the user input device is a rotary switch that is configured to rotate along the range of positions, and wherein the discontinuous single state zone is defined over a subset of a total rotational range of the user input device.

3. The agitator of claim 1, wherein the user input device comprises a non-detent switch.

4. The agitator of claim 1, wherein the range of positions includes a continuous zone in which a plurality of adjacent positions of the range of positions correspond to different oscillation speeds for the frame, and wherein the continuous zone is adjacent the discontinuous single state zone.

5. The agitator of claim 4, wherein the continuous zone is a first continuous zone, wherein the range of positions includes a second continuous zone in which a plurality of adjacent positions of the range of positions correspond to different oscillation speeds for the frame, and wherein the discontinuous single state zone is located between the first continuous zone and the second continuous zone along the range of positions.

6. The agitator of claim 1, further comprising a memory device in communication with the controller and that is configured to store data from a plurality of sensors coupled to the agitator.

7. The agitator of claim 6, wherein each of the plurality of sensors is in communication with the controller and is configured to communicate an independent speed to the controller.

8. The agitator of claim 1, wherein the driver includes a motor having an output shaft coupled to an arm that is configured to move the frame relative to the base.

9. The agitator of claim 1, wherein the controller is configured to monitor and control the oscillation speed of the frame relative to the base.

10. The agitator of claim 7, wherein the agitator is configured to oscillate at a rate that is sufficient to prevent coagulation of the platelets located in the agitator.

11. The agitator of claim 1, wherein the agitator includes a sensor in communication with the controller, and wherein the controller is configured to monitor the speed of oscillation of the frame of the agitator relative to the base of the agitator by use of the sensor.

12. The agitator of claim 1, wherein the controller is configured to store a log of events.

13. The agitator of claim 12, wherein the log includes a date of the event, a time of the event, and a measured speed of oscillation of the agitator during the event.

14. An agitator, comprising:
a base;
a frame coupled to the base such that the frame is configured to oscillate relative to the base;
a controller;
a memory device in communication with the controller;
a driver in communication with the controller that is configured to oscillate the frame relative to the base;
a user input device in communication with the controller and actuatable through a range of positions that correspond to a range of available oscillation speeds for the frame, wherein the range of positions includes a discontinuous single state zone in which a plurality of adjacent positions of the range of positions correspond to a single oscillation speed for the frame, and wherein the controller is configured to receive a signal from the user input device corresponding to a selected oscillation speed from the range of oscillation speeds and, in response, provide a signal to the driver to operate at the selected oscillation speed; and
an at least one sensor in communication with the controller.

15. The agitator of claim 14, wherein the controller comprises a processor and the memory device includes instructions that, when executed by the processor, cause the controller to control the speed of oscillation of the frame relative to the base via the driver.

16. The agitator of claim 15, wherein the processor is configured to use a feedback control system to control the speed of oscillation of the frame relative to the base.

17. The agitator of claim 16, wherein the feedback control system is a proportional-plus-integral-plus-derivative controller.

18. The agitator of claim 15, wherein the controller is configured to log an event if the frame fails to oscillate at a selected speed relative to the base.

19. The agitator of claim 15, wherein the controller is configured to receive a user input alarm condition for an operational parameter, wherein the controller is further configured to log an event if the alarm condition is met.

20. The agitator of claim 19, wherein the operational parameter includes the speed of oscillation of the frame relative to the base.

21. A control system for a variable speed agitator, the control system comprising:
a controller having a processor and a memory device;
a variable speed driver in communication with the controller;
a user input device in communication with the controller, the user input device having a range of adjustments that correspond to a range of oscillation speeds for the agitator, the range of adjustments being discontinuous such that a portion of the range is linear and a portion of the range is non-linear; and
wherein the controller is configured to receive a signal from the user input device corresponding to a selected oscillation speed from the range of oscillation speeds and, in response, the processor is configured to process the signal using instructions from the memory device and to provide a signal to the variable speed driver to drive the variable speed driver at the selected oscillation speed.

22. The control system of claim 21, wherein the user input device is configured such that an oscillation speed of the agitator is changed linearly through the linear portion of the range of the user input device.

23. The control system of claim 22, wherein the oscillation speed of the agitator is maintained at a constant speed through the non-linear portion of the range.

24. A control system for a variable speed agitator, the control system comprising:
a controller having a processor and a memory device;
a variable speed driver in communication with the controller;
a user input device in communication with the controller, the user input device having a range of adjustments that correspond to a range of oscillation speeds of the agitator, the range of adjustments having a first zone covering a plurality of first adjustments within the range of adjustments and a second zone covering a plurality of second adjustments within the range of adjustments, each of the plurality of first adjustments corresponding to a different oscillation speed, and all of the plurality of second adjustments corresponding to a single oscillation speed; and
wherein the controller is configured to receive a signal from the user input device corresponding to a selected oscillation speed from the range of oscillation speeds and, in response, the processor is configured to process the signal using instructions from the memory device and to provide a signal to the variable speed driver to control the variable speed driver at the selected oscillation speed.

25. The control system of claim 24, wherein the user input device is a rotary switch that is rotatably along the range of adjustments.

26. The control system of claim 24, wherein the user input device comprises a non-detent switch.

27. The control system of claim 24, wherein the first zone is adjacent the second zone along the range of adjustments.

28. The control system of claim 24, wherein the range of adjustments has a third zone covering a plurality of third adjustments of the range of adjustments, and wherein each of the plurality of third adjustments correspond to a different oscillation speed of the agitator.

29. The control system of claim 28, wherein the second zone is positioned between the first zone and the third zone along the range of adjustments.

\* \* \* \* \*